US007038774B2

(12) United States Patent
Hazen et al.

(10) Patent No.: US 7,038,774 B2
(45) Date of Patent: May 2, 2006

(54) METHOD OF CHARACTERIZING SPECTROMETER INSTRUMENTS AND PROVIDING CALIBRATION MODELS TO COMPENSATE FOR INSTRUMENT VARIATION

(75) Inventors: Kevin H. Hazen, Gilbert, AZ (US); Thomas B. Blank, Chandler, AZ (US); Stephen Monfre, Gilbert, AZ (US); Timothy L. Ruchti, Gilbert, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 0 days.

(21) Appl. No.: 10/870,727

(22) Filed: Jun. 16, 2004

(65) Prior Publication Data

US 2004/0223155 A1   Nov. 11, 2004

Related U.S. Application Data

(60) Division of application No. 09/664,973, filed on Sep. 18, 2000, now Pat. No. 6,864,978, which is a continuation-in-part of application No. 09/359,191, filed on Jul. 22, 1999, now Pat. No. 6,280,381.

(51) Int. Cl.
*G01J 3/28* (2006.01)
(52) U.S. Cl. .................................................... 356/326
(58) Field of Classification Search ......... 356/300–334
See application file for complete search history.

(56) References Cited

U.S. PATENT DOCUMENTS

| 5,243,546 | A | * | 9/1993 | Maggard ...................... 702/90 |
| 5,446,681 | A | * | 8/1995 | Gethner et al. ................ 702/27 |
| 5,459,677 | A | * | 10/1995 | Kowalski et al. ............... 703/2 |
| 5,710,713 | A | * | 1/1998 | Wright et al. ................ 250/282 |
| 5,857,462 | A | * | 1/1999 | Thomas et al. ............. 600/310 |
| 5,976,466 | A | * | 11/1999 | Ratner et al. ............ 422/82.11 |
| 6,549,861 | B1 | * | 4/2003 | Mark et al. ................... 702/76 |
| 6,615,151 | B1 | * | 9/2003 | Scecina et al. ............... 702/85 |

* cited by examiner

*Primary Examiner*—Samuel A. Turner
*Assistant Examiner*—Gordon J. Stock, Jr.
(74) *Attorney, Agent, or Firm*—Michael A. Glenn; Glenn Patent Group

(57) ABSTRACT

Spectrometer instruments are characterized by classifying their spectra into previously defined clusters. The spectra are mapped to the clusters and a classification is made based on similarity of extracted spectral features to one of the previously defined clusters. Calibration models for each cluster are provided to compensate for instrumental variation. Calibration models are provided either by transferring a master calibration to slave calibrations or by calculating a separate calibration for each cluster. In one embodiment, a simplified method of calibration transfer maps clusters to each other, so that a calibration transferred between clusters models only the difference between the two clusters, substantially reducing the complexity of the model.

17 Claims, 4 Drawing Sheets

METHOD OF CHARACTERIZING SPECTROMETER INSTRUMENTS AND PROVIDING CALIBRATION MODELS TO COMPENSATE FOR INSTRUMENT VARIATION

CROSS-REFERENCE TO RELATED APPLICATION

This application is a divisional application of U.S. patent application Ser. No. 09/664,973 filed Sep. 18, 2000 now U.S. Pat. No. 6,864,978, which is a continuation-in-part of U.S. patent application Ser. No. 09/359,191 filed Jul. 22, 1999, now U.S. Pat. No. 6,280,381 (Aug. 28, 2001).

BACKGROUND OF THE INVENTION

1. Field of the Invention

The invention relates to variations in spectrometer instruments. More particularly the invention relates to characterizing spectrometer instruments by classifying their spectral responses into a limited number of clusters and developing calibration transfer models between clusters that compensate for instrument variations.

2. Description of the Prior Art

Many of the analytical applications for spectrometers require calibration data sets that are time-consuming and expensive to create. Typically, these calibrations are highly specific. For example, apparently identical instruments produced by the same manufacturer may exhibit minor instrument variations. Such variations may be seen when one instrument is built with a component that varies slightly from the same component in another instrument. In addition, a calibration set for an instrument produced by one manufacturer is generally not suitable for a similar instrument produced by another manufacturer. Furthermore, repairs to a single instrument can cause the instrument's spectral response to vary. An instrument's spectral response may change as it ages. An instrument's spectral response may also vary according to fluctuations in the operating environment. In applications requiring analysis of very low concentration analytes, non-invasive blood glucose prediction, for example, even minor instrument variation can introduce an unacceptable degree of error into the analysis. Providing another calibration model that takes the instrument's current spectral response into account can compensate for instrument variation. However, development of new calibration models is time-consuming, labor-intensive, and costly.

In the development of spectroscopy-based analyzers for biomedical applications, there is a need for production of thousands to as many as millions of analyzers for a specific application. No methodology exists for providing calibrations for large numbers of instruments quickly and inexpensively.

Therefore, efforts have been directed at transferring calibrations from one analyzer to another. See, for example, E. Bouveresse, C. Hartmann, D. Massart, I. Last, K. Prebble, *Standardization of near-infrared spectrometric instruments*, Anal. Chem., vol. 68, pp. 982–990 (1996); M. Defernez, R. Wilson, *Infrared spectroscopy: instrumental factors affecting the long-term validity of chemometric models*, Anal. Chem., vol. 69, pp. 1288–1294 (1997); E. Bouveresse, D. Massart, P. Dardenne, *Calibration transfer across near-infrared spectrometric instruments using Shenk's algorithm: effects of different standardization samples*, Analytica Chimica Acta, vol. 297, pp. 405–416, (1994); and Y. Wang, D. Veltkamp, B. Kowalski, *Multivariate instrument calibration*, Anal. Chem., vol. 63, pp. 2750–2756 (1991).

Most of the reported methods of calibration transfer have been applied in situations involving high-concentration analytes, wherein the signal-to-noise ratio is high. Because these currently known methods act as a smoothing function when transferring calibrations, they degrade the signal to noise that can be observed, thus hindering analysis of low concentration analytes. Additional problems of changes in resolution or bandwith across time or between instruments have not been addressed.

Furthermore, the currently known methods have only been successfully applied in situations involving a small number of instruments. The reported methods are not capable of modeling the complexity encountered when large numbers of instruments are involved.

A need exists for the calibration of large numbers of analyzers. It would be desirable to provide a means of reducing the complexity inherent in the transfer of calibrations to large numbers of analyzers. It would also be advantageous to provide a means of transferring calibrations without significant degradation of the signal-to-noise ratio, rendering calibration transfer practical in analysis of low concentration analytes.

SUMMARY OF THE INVENTION

The invention provides a method of characterizing large numbers of spectrometer instruments by classifying their spectra into a limited number of previously defined clusters according to similarity of spectral features and performance characteristics. The method may also be used to track variations over time within a single instrument. The spectral features used for classification may be related to known instrument parameters, or they may be abstract features derived using a variety of computational methods. The clusters are defined in advance based on an exemplar data set, using either supervised or unsupervised methods. Calibration models for each cluster compensate for instrument variation, either across instruments or across time within a single instrument.

In a preferred embodiment of the invention, calibration models are provided using a method of calibration transfer wherein the clusters are mapped to each other, so that a calibration transferred from one cluster to another need only model the difference between the two clusters. In an alternate embodiment, a different calibration is separately calculated for each cluster. In either embodiment, the number of calibration transfers is significantly reduced since each cluster represents a multitude of instruments.

DETAILED DESCRIPTION

The invention provides a method of characterizing spectrometer instruments by classifying spectral responses from a large number of spectrometers (analyzers) into a limited number of previously defined clusters. The clusters constitute groups that are defined based on the similarity of specific features. Grouping of instruments according to spectral features and performance characteristics reduces the spectral variation between instruments in a given group. Therefore, spectral measurements corresponding to an individual cluster are more homogeneous than those from the entire group of analyzers. Calibrations created for each cluster may then be used for subsequent analysis. The calibration created for a cluster has instrument variations included in the model that mirror variations resulting from the particular analyzer employed for the subsequent analysis. Calibration models specific to the clusters are expected to be less complex and have an improved level of accuracy. Therefore, multivariate analysis requires fewer factors to model instrument variation resulting in earlier factors modeling the sample and earlier factors modeling small absorbing analytes. The net result is that fewer factors are required for sample analysis and a more robust algorithm is created.

In one embodiment of the invention, a separate calibration data set is required for every cluster, requiring a large number of samples in a calibration set for every cluster. In the preferred embodiment, sufficient samples for a calibration model are only required in a single cluster. Principal features defining that cluster and other clusters are determined, and the clusters are mapped to each other, revealing the specific differences from one cluster to another. Subsequently, the calibration from the initial cluster is transferred to another cluster based upon the specific differences between clusters.

The parent application to the current application, S. Malin and T. Ruchti, An intelligent system for noninvasive blood analyte prediction, U.S. patent application Ser. No. 09/359,191 (Jul. 22, 1999), provides a detailed description of a method of classifying spectral measurements into previously defined clusters through similarities observed in absorbance spectra. The classification system of the sampled tissue volume of the subjects is herein expanded to include classification of instrumentation variations.

Figure 1:
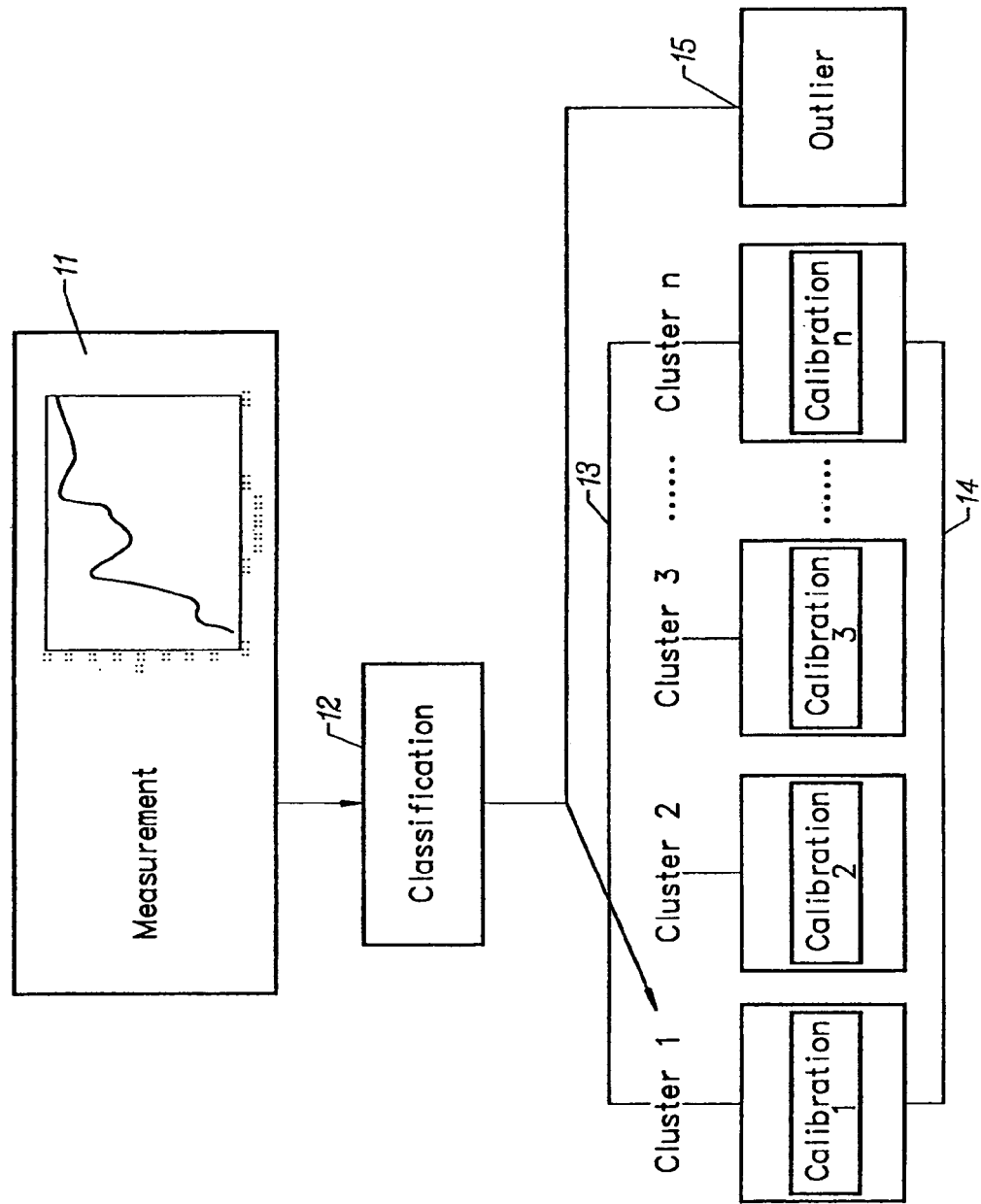
FIG. 1 provides a block schematic diagram of a method of characterizing spectrometer instruments by clustering according to spectral features according to the invention.

Referring now to FIG. 1, a general method of classifying spectral measurements into previously defined clusters is represented. Briefly the steps of the method are:

1. Measurement (11).
2. Classification (12), in which the measured spectrum is assigned membership in any one of a number of predefined clusters (13).
3. Calibration (14), in which calibration models suited to each cluster are provided.
4. Identifying outliers (15).

Measurement

In general, instrumental variations may affect spectral response by producing either signal intensity changes, bandwidth changes, wavelength changes, or combinations thereof. These instrumental variations may include:

1. wavelength shifts;
2. nonlinear wavelength shifts;
3. wavelength expansions;
4. wavelength contractions;
5. nonlinear wavelength expansions;
6. source intensity drifts;
7. blackbody profile changes;
8. bandwidth changes;
9. resolution changes;
10. baseline deviations;
11. change with time;
12. temperature effects;
13. detector response;
14. differences in optical components, e.g. long-pass filters or fiber optics;
15. variation related to mounting of references;
16. differences in the optical interface to the sample (fiber spacing);
17. linearity; and
18. detector cut-off;

and many others, which will be apparent to those skilled in the art. Spectra used for classification are typically those of commonly known standards. Standards particularly useful for classifying shifts observed in the wavelength axis include polystyrene, rare earth oxides: holmium oxide, erbium oxide or dysprosium oxide, for example; or combinations thereof. Standards, such as the diffuse reflectance standards supplied by Labsphere, Inc. (North Sutton N.H.), may be used to classify shifts in the intensity axis. Spectra of samples may also be used for classification. Additional intensity and wavelength standards will be known to those skilled in the art.

In the specific case of near-IR noninvasive glucose determination these standards cover the near-IR spectral region. Additional spectroscopy and chromatography-spectroscopy hyphenated techniques such as AA (atomic absorption spectroscopy) or GC-MS (gas chromatography mass spectroscopy) each require their own standards, which are known by those skilled in the art. Additionally, spectra of tissue phantoms collected on an instrument may also be used to characterize that instrument. Tissue phantoms are helpful in characterizing an instrument because spectra of these phantoms simulate noninvasive spectra of living tissue. There are tissue phantoms that simulate the absorption coefficients of various skin tissues, while others simulate the scattering coefficients of the body. Some common simulants include:

1. milk and milk products;
2. milk products in combination with India ink, used to adjust the absorption coefficient;
3. emulsions of fatty substances in water maintained in solution with an emulsifier such as lecithin. One such commercial product is INTRALIPID, supplied by Kabivitrum AB (Stockholm, Sweden); and
4. Intra-serum and Intra-gel. See K. Hazen, J. Welch, S. Malin, T. Ruchti, A Lorenz, T. Troy, S. Thenadil, T. Blank, Intra-serum and intra-gel for modeling human skin tissue, U.S. patent application Ser. No. 09/502,877 (Feb. 10, 2000).

Other scattering and absorbing mediums are known to those skilled in the art. Concentrations of these tissue simulants may be adjusted to match the scattering and absorption coefficients of body tissues such as skin or internal organs.

It will also be apparent that a set of exemplar measurements is required for cluster definition and development of calibration models, in addition to the actual spectral measurements used for classification.

Classification

New spectral measurements are passed to a pattern classification system that classifies the measurements into previously defined clusters having a high degree of internal constistency through spectral features related to instrumental variation.

The classification itself includes the following steps:
1. Feature extraction; and
2. Classification of features according to a classification model.

Feature Extraction

The process of feature extraction is more fully described in the parent application to the current application, U.S. patent application Ser. No. 09/359,191, supra. Feature extraction is any mathematical transformation that enhances a particular aspect or quality of the data that is useful for interpretation. Features may be of two categories:
1. Abstract; and
2. Simple.

Instruments may be classified by abstract features, meaning that they may be classified using computational methods. These methods may be supervised or unsupervised. Examples include plotting primary principal components versus one another and identifying clusters of results; discriminant analysis, such as measurement of the Mahalanobis distance, and k-means clustering. Additional methods will be readily apparent to those skilled in the art.

It is important to note that the clustering techniques listed above are not mutually exclusive. Clustering of raw spectra into one or more groups may be achieved through one or more of these methods and with combinations of these approaches.

Simple features are derived from an a priori understanding of the system, and can be related directly to an instrument parameter or component (or parameters or components). For example, the measured bandwith, noise characteristics, or linearity and detector cutoffs.

Cluster Definition

As indicated above, clusters must have been previously defined, using a data set of exemplar spectral measurements. Cluster definition is the assignment of the measurements in the exploratory data set to clusters. After cluster definition, the measurements and class assignments are used to determine the mapping from the features to cluster assignment.

Cluster definition is performed using either supervised or unsupervised methods. In the supervised case, clusters may be defined using specific knowledge of the system. For example, source intensity and detector temperatures have specific effects on the spectra, as demonstrated further below. The use of a priori information in this manner is the first step in supervised pattern recognition, which develops classification models when the class assignment is known.

Alternatively, clusters may be defined in an unsupervised manner using abstract features such as clustering within plots of principal component scores 'x' versus spectral loading 'y'. The result is that within a given cluster, all of the spectra have the same characteristics (interferences, instrument variations, or sample issues). Clusters formed from features with physical meaning can be interpreted based on the known underlying phenomenon causing variation in the feature space.

Classification

Subsequent to class definition, a classifier is designed through supervised pattern recognition. A model is created, based on cluster definitions, that transforms a measured set of features to an estimated classification. The classification model is a method for determining a set of similarity measures with the predefined clusters. A decision rule assigns membership on the basis of a set of measures calculated by a decision engine.

Calibration

Once the spectra have been classified into clusters, calibration models 14 (FIG. 1) are required for each cluster. Provision of the clusters is by one of two methods. In the preferred embodiment, a master calibration is developed for a first cluster, subsequently the master calibration is transferred to slave calibrations, one for each remaining cluster. An alternate embodiment, described further below, individually calculates calibrations for each cluster.

In the case of spectra collected using a master and slave instrument, the term "calibration transfer," as commonly used in the art, may have different meanings. Calibration transfer may refer to transforming the slave spectral to look like the master spectra or vice versa. Additionally, spectra from both the master and the slave can be transferred to a common standard spectrum not present in the master or slave data sets. Furthermore, calibration transfer can refer to preprocessing steps, multivariate adjustments of the sample spectra, or adjustments to the predicted analyte concentrations based upon standards.

Figure 2:
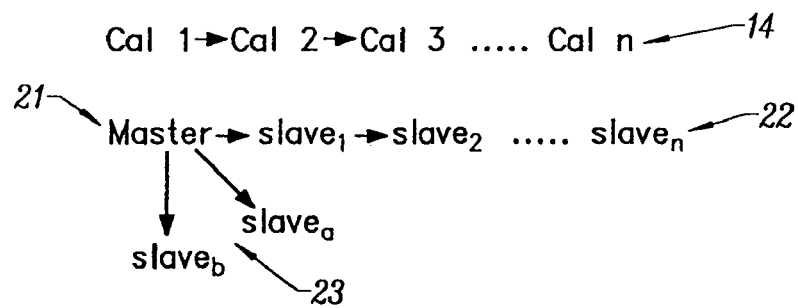
FIG. 2 provides a flow diagram of a method of generating calibration models by transferring a master calibration to slave calibration models according to the invention.

Referring now to FIG. 2, the process of calibration transfer is shown. Calibrations 14 are required for each of n clusters. A master calibration 21 is calculated for a first cluster. Then, the master calibration is transferred to slave calibrations to provide calibrations for each of the remaining n clusters. In this case, calibration transfer refers to the process of transforming spectra on a slave instrument to match the characteristics of the master such that the master calibration can be applied to the slave spectra. For clusters, calibration transfer refers to the process of transforming spectra on a slave instrument to match the characteristics of the master, such that a new calibration is generated that satisfies the specification of a cluster other than the one for which the master cluster was developed.

The clusters may also be organized into groups of clusters, so that the master calibration is transferred to slave calibrations 23, which in turn are transferred to the slave calibration for the various clusters within each group.

Prior art methods of calibration transfer have been unsuccessful at modeling the complexity involved in providing calibration models for large numbers of instruments. Classifying the spectral measurements into clusters having a high degree of internal consistency reduces the complexity of the problem to a level that makes it possible to apply calibration transfer to large numbers of instruments. Clustering the acquired spectra into a limited number of subgroups allows the calibration transfer issues to be broken up into subsets, so that only a subset of the overall issues needs to be addressed between any two clusters. The result is that within a given cluster, all of the spectra have the same characteristics. A calibration is generated for a given cluster using spectra of samples containing the limited number of characteristics of that cluster. This eliminates having to deal with all of the variations possible in the raw measurements, significantly reducing the complexity that needs to be modeled by the calibration. Thus, the calibration used for a given cluster has instrument variations included in the model that are similar to variations resulting from the analyzer employed. Because each cluster has its own specification, the calibration transfer technique need only concern the differences between those two clusters. For example, if the only difference between the clusters is a linear x-axis shift, then the calibration transfer technique need only concern that parameter. This allows a more specific calibration transfer technique to be employed that is more robust, resulting in fewer factors because fewer instrument variations need to be modeled. This results in analysis of lower concentration analytes due to retention of signal to noise in the calibration transfer step.

Typically, calibration transfer techniques have to address instrument-to-instrument variations, such as wavelength shifts, nonlinear wavelength shifts, wavelength expansions (contraction), nonlinear wavelength expansions, source intensity drifts, blackbody profile changes, bandwidth (resolution) changes, baseline deviations, change with time, temperature effects, and others known to those skilled in the art.

However, in addition to instrumentation issues in calibration transfer, sample composition and sample handling considerations are very important in calibration transfer. Therefore, every sample analyzed for prediction of results should be an interpolation within the matrix space of the calibration data set. Otherwise, the calibration may not calculate an accurate prediction of analyte concentration. For example, if the calibration data set contains glucose samples ranging from 40 to 400 mg/dL, then predictions on samples with glucose outside of this range are suspect.

Thus, an important additional benefit of the invented classification algorithm is that outlier spectra may be identified, as shown in FIG. 1. Each cluster has its own set of classification requirements. If a spectrum does not fall within the parameters of a given cluster, another cluster must be found which has parameters allowing analysis of that spectrum. If no cluster is found, then the sample is reported as an outlier rather than having a value reported for the analyte that may not be correct. In this manner, analysis on samples or instruments for which no satisfactory calibration model has been developed is prevented.

Spectra classified as outliers may assume two forms. In some instances, the outlier spectrum is close to a given cluster. In such a case, conventional calibration transfer techniques may be applied to this spectrum to transform the spectrum, such that it falls within one of the clusters for which calibrations exist. In case of failure, the spectrum remains classified as an outlier, as are spectra that are characterized as gross outliers.

Classification and calibration transfer need not be limited to differences in instrumentation. It may also be applied to sample spectra for analyte prediction. For example, a cluster may be defined for healthy 18 to 30 year old men. A noninvasive glucose model may be built for this narrow demographic. A separate cluster may be for 18 to 30 year old non-pregnant women. Differences between the two clusters, such as body fat and sampled volume, may be addressed and a calibration transfer technique may be optimized for those differences based on relatively few spectra, thus allowing a glucose model initially generated for a narrow demographic to be gradually expanded.

The foregoing embodiment does not require calibrations to be built for every cluster, and thereby provides the important advantage of sparing the considerable time, money, and effort required for building a separate calibration for every cluster. The actual calibration transfer technique employed may be selected from the many algorithms known to those skilled in the art.

An alternative embodiment classifies spectra into clusters, as in the preferred embodiment, and builds individual calibrations for each cluster. The requirement for calibration transfer is eliminated at the expense of the requirement for more spectra. However, an additional measure of reliability is gained by having clusters with well-defined and narrow parameters. As in the previous embodiment, fewer instrument variations need to be modeled so that early factors can focus on analyte information, resulting in a more robust model.

While the foregoing description of the invention has been directed to characterizing different instruments, the invented method also finds application in classifying spectra from a single instrument according to known variations in instrument components or known environmental variations. Two examples are described.

Figure 3A:
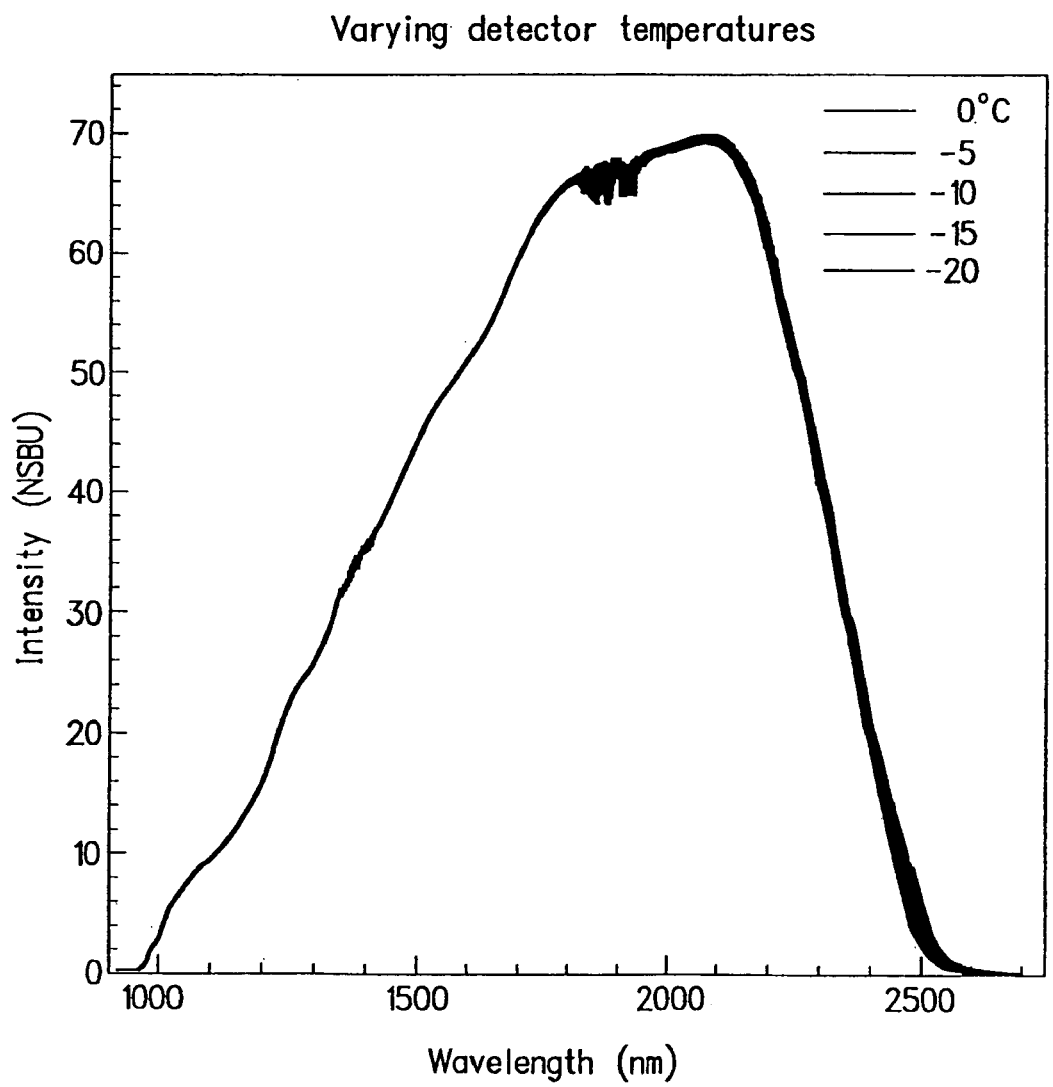
FIGS. 3A and 3B illustrate decreases in spectral cutoff related to decreases in detector temperature in a spectrometer instrument.
Figure 3B:
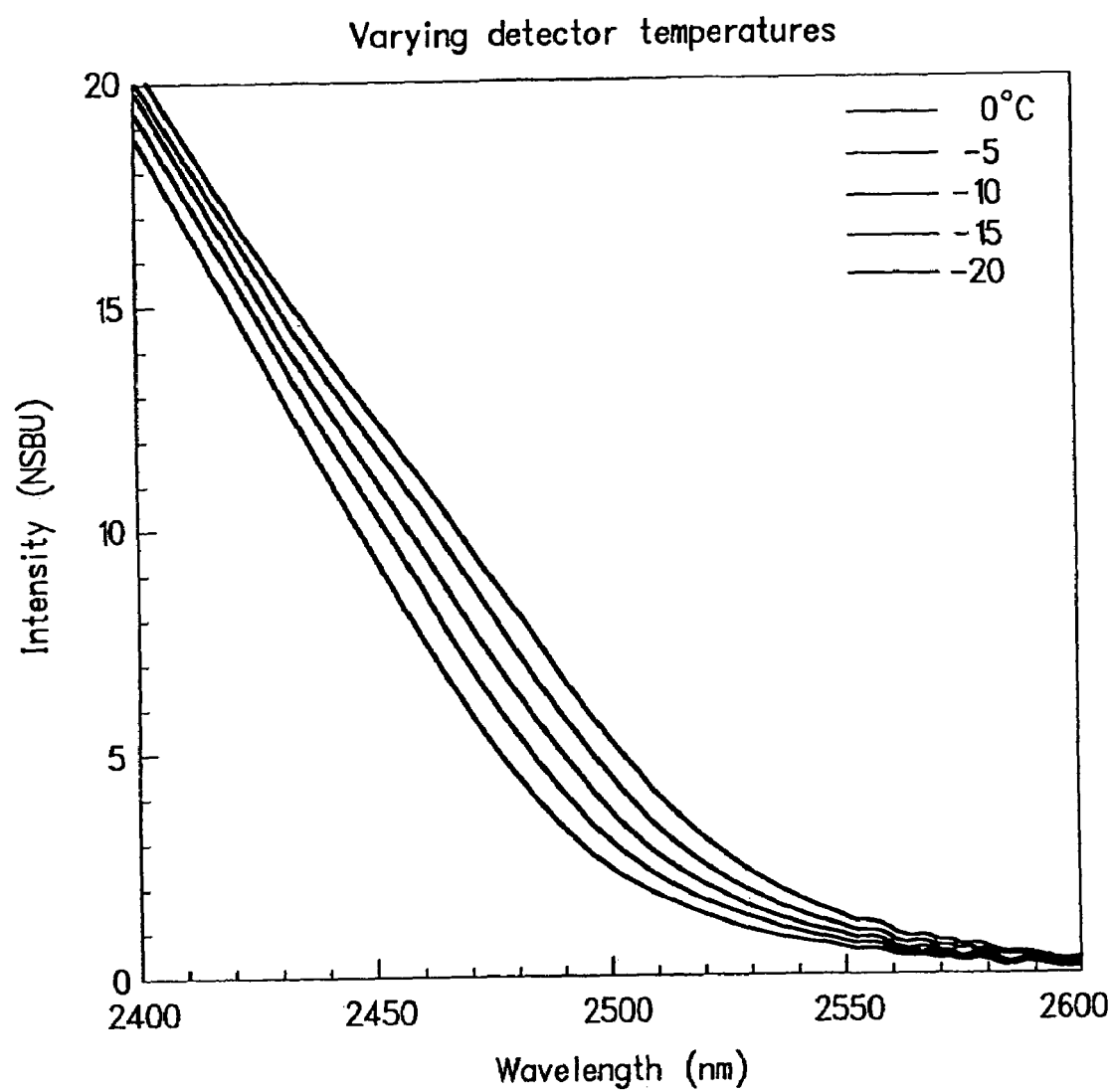

1. The cutoff of the 2.6_m InGaAs detector employed in many near-IR analyzers blue shifts as the temperature of the detector decreases. Air spectra collected on a NICOLET 860, supplied by the Nicolet Instrument Corporation (Madison Wis.) with the InGaAs detector ranging from 0 to −20° C. are presented in FIG. 3A. The spectral cutoff region from 2400 to 2600 nm is expanded in FIG. 3B. The cut-off decreases as the detector temperature decreases. Using reference or air spectra, a simple analysis, such as determining the wavelength at which 10% of the peak intensity is observed, allows the instrument to be classified as to whether the detector is properly cooled and to the extent that it was cooled.

Figure 4:
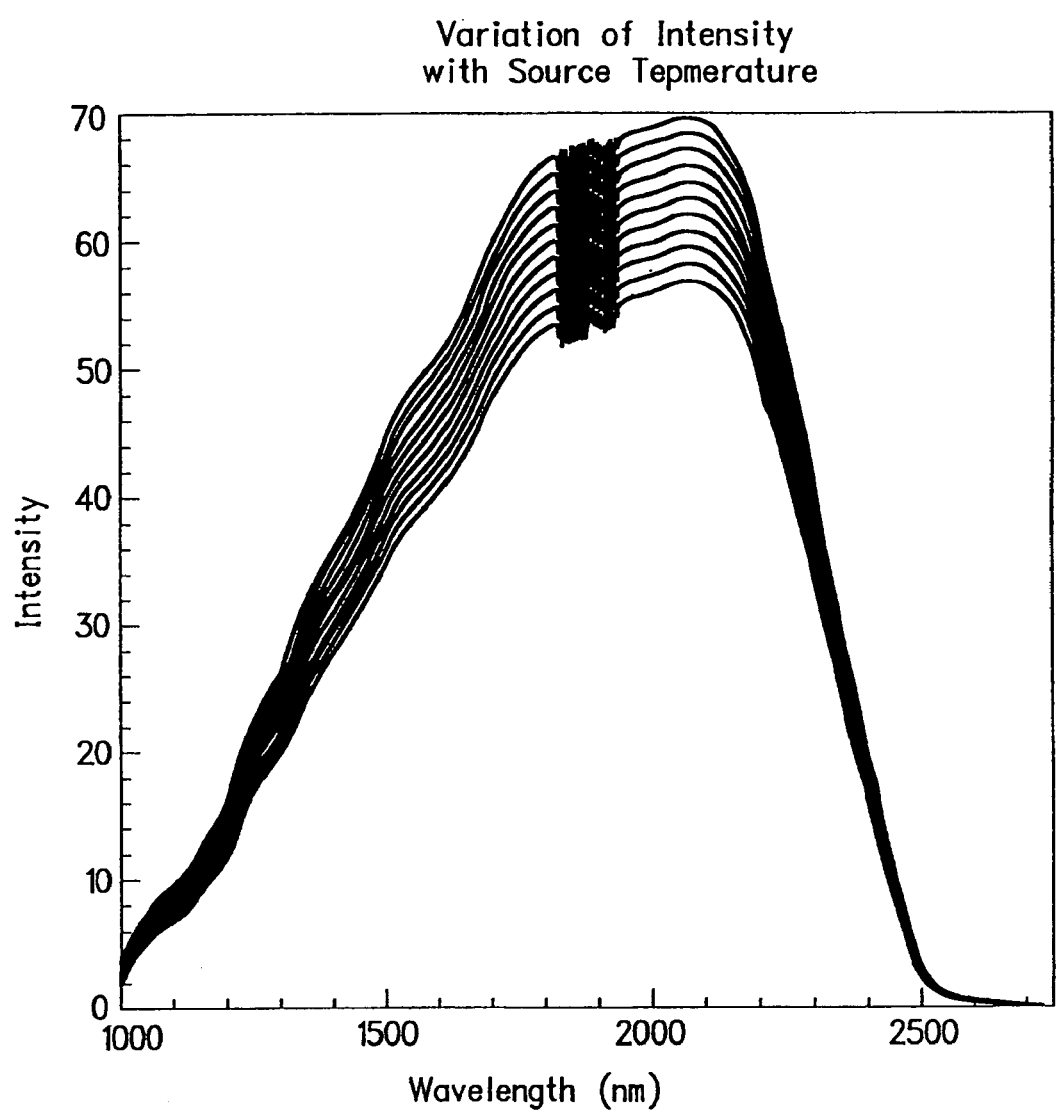
FIG. 4 illustrates changes in light throughput related to changes in source temperature in a spectrometer instrument.

2. As a tungsten halogen source increases in temperature, the blackbody emission increases in magnitude and additional light throughput is observed. For example, in diffuse reflectance spectra of a 5% Labsphere diffuse reflectance standard, the overall intensity is observed to increase as the source temperature increases, as shown in FIG. 4. This effect can be used to classify the instrument in terms of the source temperature and total light throughput.

It is a relatively simple task to characterize the instrument in terms of additional components. Examples are slit width, affecting bandwidth or room temperature, affecting total light throughput. There are, however, a limited number of components to a spectrometer. It has been observed that instruments group into a relatively small number of clusters.

Once an instrument, or a given spectrum, is classified into a cluster, the appropriate calibration routine can be employed. A single analyzer may be loaded with multiple calibration routines because the instrument may vary during its lifetime. In fact, environmental factors may cause the appropriate calibration to change with every spectrum collected. In some embodiments, these factors may be monitored by the instrument and may not be used to select an appropriate calibration in real time.

This instrument classification approach was designed for use on noninvasive glucose analyzers where glucose is measured using diffuse reflectance spectra of skin on the human body. However, the same technology can be applied to any form of noninvasive analysis including but not limited to: noninvasive analysis of albumin, globulin, urea, creatinine, oxygen, hemoglobin $A_1C$, and electrolytes such as $Na^+$, $K^+$, $Cl^-$. The technology may also be used in biomedical, industrial, and agricultural applications.

The classification approach disclosed here finds application in various fields of endeavor, the agricultural field, for example. Exemplary agricultural applications are: analysis of fat in milk, protein or moisture analysis in wheat, or analysis of sugars in fruits. The classification approach may also benefit pharmaceutical companies in the analysis of intact tablets or in the characterization of raw materials. Finally, petrochemical companies may use the method in classification of fuels, fuel by-products, and in raw fuel materials. In general, this technique is useful wherever a large number of analyzers are used to quantify analytes in samples.

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

The invention claimed is:

1. A method for generating an analyte prediction, comprising the steps of:
    collecting a sample spectrum;
    providing a plurality of predefined clusters with corresponding calibration models, wherein each cluster is characterized according to spectral features representative of states of at least one spectrometer instrument;
    mapping said sample spectrum to one of said predefined clusters; and
    applying said corresponding calibration model to generate said analyte prediction.

2. The method of claim 1, wherein said states comprise any of:
    variation of a single spectrometer over time; and
    variation between spectrometers.

3. The method of claim 1, further comprising the step of:
    classifying said at least one spectrometer instrument into at least one of said clusters.

4. The method of claim 3, said step of classifying comprising:
    extracting features; and
    classifying said features according to a classification model and decision rule.

5. The method of claim 4, wherein said feature extraction step comprises:
    applying a mathematical transformation to enhances a particular aspect or quality of data that is useful for interpretation.

6. The method of claim 4, wherein individual features are divided into two categories, said categories comprising:
    abstract features, wherein said features are extracted using various computational methods; and
    simple features that are derived from an a priori understanding of a system, wherein said feature is directly related to an instrument parameter or component.

7. The method of claim 1, wherein said step of mapping said sample spectrum to one of said predefined clusters comprises:
    associating said sample spectrum to one of said predefined clusters.

8. The method of claim 7, further comprising the step of:
    reporting said sample spectrum as an outlier if a matching cluster is not found.

9. An apparatus for generating an analyte prediction, comprising:
    means for collecting a sample spectrum;
    means for a plurality of predefined clusters having corresponding calibration models, wherein each cluster is characterized according to spectral features representative of states of at least one spectrometer instrument;
    means for mapping said sample spectrum to one of said predefined clusters; and
    means for applying a corresponding calibration model to generate said analyte prediction.

10. The apparatus of claim 9, wherein said states comprise any of:
    variation of a single spectrometer over time; and
    variation between spectrometers.

11. The apparatus of claim 9, further comprising:
    means for classifying said at least one spectrometer instrument into at least one of said clusters.

12. The apparatus of claim 11, said means for classifying further comprising:
    means for extracting features; and
    means for classifying said features according to a classification model and decision rule.

13. The apparatus of claim 12, wherein said feature extraction means comprises:
    a mathematical transformation for enhancing a particular aspect or quality of data that is useful for interpretation.

14. The apparatus of claim 12, wherein individual features are divided into two categories, said categories comprising:
    abstract features, wherein said features are extracted using various computational methods; and
    simple features that are derived from an a priori understanding of a system, wherein said feature is directly related to an instrument parameter or component.

15. The apparatus of claim 9, wherein said mapping means comprise:
    associating said sample spectrum to one of said predefined clusters.

16. The apparatus of claim 15, further comprising:
    means for reporting said sample spectrum as an outlier if a matching cluster is not found.

17. An apparatus for characterizing a spectrometer instrument, comprising:
    a plurality of predefined clusters having corresponding calibration models;
    wherein each cluster is characterized according to spectral features representative of states of at least one spectrometer instrument; and
    means for mapping a sample spectrum obtained by said spectrometer instrument to one of said predefined clusters.

* * * * *